United States Patent [19]

Han et al.

[11] Patent Number: 5,191,138

[45] Date of Patent: Mar. 2, 1993

[54] PROCESS FOR OXIDATIVE CONVERSION OF METHANE TO HIGHER HYDROCARBONS USING METAL SULFIDE OXIDIZING AGENT

[75] Inventors: Scott Han, Lawrenceville; James N. Michaels, Neshanic Station; Robert E. Palermo, Bloomfield, all of N.J.; David L. Stern, Yardley; Dennis E. Walsh, Richboro, both of Pa.

[73] Assignee: Mobil Oil Corp., Fairfax, Va.

[21] Appl. No.: 794,560

[22] Filed: Nov. 19, 1991

Related U.S. Application Data

[63] Continuation-in-part of Ser. No. 597,217, Oct. 15, 1990, abandoned.

[51] Int. Cl.$^5$ .................................................. C07C 1/00
[52] U.S. Cl. ................................... 585/500; 585/415; 585/417; 585/418; 585/654; 585/658; 585/661; 585/700; 585/943; 585/541; 585/820; 585/822
[58] Field of Search ............... 585/415, 417, 418, 654, 585/658, 661, 700, 943, 500, 541, 820, 822

[56] References Cited

U.S. PATENT DOCUMENTS

| | | | |
|---|---|---|---|
| 4,465,893 | 8/1984 | Olah | 585/709 |
| 4,543,434 | 9/1985 | Chang | 585/310 |
| 4,751,336 | 6/1988 | Jezl et al. | 585/324 |
| 4,754,093 | 6/1988 | Jezl et al. | 585/500 |
| 4,822,938 | 4/1989 | Audeh et al. | 585/324 |
| 4,864,073 | 9/1989 | Han et al. | 585/943 |
| 4,864,074 | 9/1989 | Han et al. | 585/943 |
| 4,879,427 | 11/1989 | Sofranko | 585/500 |

FOREIGN PATENT DOCUMENTS

0225185 6/1987 European Pat. Off. .

*Primary Examiner*—Patrick P. Garvin
*Assistant Examiner*—E. D. Irzinski
*Attorney, Agent, or Firm*—Alexander J. McKillop; Charles J. Speciale; Edward F. Kenehan, Jr.

[57] ABSTRACT

There is provided a process for converting methane to hydrocarbons having at least two carbon atoms (i.e. higher hydrocarbons). The process involves oxidizing methane with a metal sulfide oxidizing agent. After this conversion of methane, the reduced metal sulfide may be regenerated by oxidation of the reduced metal sulfide.

8 Claims, No Drawings

PROCESS FOR OXIDATIVE CONVERSION OF METHANE TO HIGHER HYDROCARBONS USING METAL SULFIDE OXIDIZING AGENT

CROSS-REFERENCE TO RELATED APPLICATION

This application is a continuation-in-part of copending U.S application Ser. No. 07/597,217, filed Oct. 15, 1990, the entire disclosure of which is expressly incorporated herein by reference.

BACKGROUND

There is provided herein a process for converting methane to hydrocarbons having at least two carbon atoms (i.e. higher hydrocarbons). The process involves contacting methane with a reducible metal sulfide. After this conversion of methane, the reduced metal sulfide may be regenerated by oxidation of the reduced metal sulfide.

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process The Mobil Oil Process, developed in the last decade provides an effective means for catalytically converting methanol to gasoline, e.g. as described in U.S. Pat. No. 3,894,107 to Butter et. al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

SUMMARY

There is provided herein a process for converting methane to at least one hydrocarbon having at least two carbon atoms, said process comprising contacting methane in the absence of $O_2$ with a reducible metal sulfide oxidizing agent under conditions sufficient to (i) produce said hydrocarbon and (ii) produce hydrogen sulfide.

EMBODIMENTS

Methane may be oxidatively upgraded to higher hydrocarbons such as ethane, ethylene, propane, etc. via a process that includes: (1) contacting methane with a reducible metal sulfide ($MS_x$) under sufficient conditions to convert a portion of the methane to higher hydrocarbons along with yielding $H_2S$ and a lower valent metal sulfide; and (2) regenerating the initial metal sulfide by an oxidation process. Alternatively, the process might be run by cofeeding methane and a suitable sulfur-atom donor over a metal sulfide catalyst.

A process is described for oxidatively converting methane to higher hydrocarbons. In the first step, methane is contacted with a suitably active, reducible metal sulfide under sufficient conditions to produce the hydrocarbon products, a lower valent metal species and $H_2S$. Equation 1 is a representative reaction for converting methane to ethane under these conditions.

$$2\ CH_4 + MS_x \rightarrow C_2H_6 + MS_{x-1} + H_2S \qquad 1$$

Similar overall reactions can produce olefins and other higher hydrocarbons (eq. 2-4)

$$2\ CH_4 + MS_x > C_2H_4 + MS_{x-2} + 2\ H_2S \qquad 2$$

$$3\ CH_4 + MS_x > C_3H_8 + MS_{x-2} + 2\ H_2S \qquad 3$$

$$3\ CH_4 + MS_x > C_3H_6 + MS_{x-3} + 3\ H_2S \qquad 4$$

The active metal sulfide can be regenerated by suitable oxidation reactions of the evolved $H_2S$ and the lower valent metal sulfide. For example, the $H_2S$ can be converted to elemental sulfur via the Claus process (eq. 5); reaction of the sulfur so produced with the lower valent metal sulfide then yields the active metal sulfide for recycling (eq. 6).

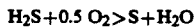

$$H_2S + 0.5\ O_2 > S + H_2O \qquad 5$$

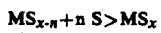

$$MS_{x-n} + n\ S > MS_x \qquad 6$$

Alternatively, the metal sulfide could be oxidized to yield a metal oxy-sulfide (eq. 7), and the resulting species then combined with $H_2$ to regenerate the starting metal sulfide (eq. 8).

$$MS_{x-n} + 0.5n\ O_2 > MS_{x-n}O_n \quad\quad 7$$

$$MS_{x-n}O_n + H_2 > MS_x + n\ H_2O \quad\quad 8$$

The overall process represented by the methane contacting step and the $MS_x$ regeneration step is the oxidative synthesis of higher hydrocarbons from methane represented by eq.9.

$$CH_4 + O_2 > C_2 + \text{products} + H_2O \quad\quad 9$$

It is also possible that the process could be run in a mode where methane and a sulfur-atom donor are co-fed to a suitable metal sulfide catalyst. Sulfur-atom donors include elemental sulfur and carbonyl-sulfide (COS). In this manner of operation, while higher hydrocarbon formation may occur through steps such as 1-4, the regeneration of the active metal sulfide occurs in in-situ via reaction with the sulfur-atom donor. The product gas is comprised of higher hydrocarbons and $H_2S$, and the sulfur-atom donor may be regenerated in an oxidative reaction to give an overall process akin to eq. 9.

This conversion represents a value uplift as these higher hydrocarbons can be more easily upgraded relative to methane, e.g., $C_2+$ hydrocarbons can be converted to gasoline range products via oligomerization/cyclization processing or dehydrocyclization processing. Inasmuch as methane is the major constituent of natural gas, these catalysts will also be useful for the analogous oxidation reaction to upgrade natural gas.

Equations 1-8 are indicative of the overall reactions and are not meant to imply any specific description of stoichiometries or mechanism. $MS_x$ represents any suitably active metal sulfide, which may be an isolated material or a supported species. Some portion of carbon from the methane may be converted to coke, and the product effluent may contain other species such as $H_2$, $CS_2$, $CS$, and organosulfur compounds.

Reaction of methane with the metal sulfide is performed under conditions sufficient to convert at least a portion of the methane to higher hydrocarbons. Reaction temperatures may be in the range of 400°-1000° C., and reaction pressures may range from 0.1-30 atmospheres. The contacting between methane and the metal sulfide may be performed in a variety of configurations including fixed bed or fluidized bed. Oxidation processes represented by equations 5 or 7 may be performed with air instead of with $O_2$.

Broad ranges for the "volume of methane feed (measured at NTP)/volume of metal sulfide/hr" in the absence of any sulfur co-feed are from about 100 to 50,000 and preferably from about 500 to 15,000. When a co-fed source of sulfur is present, the broad range for the methane/S ratio in the feed is from about 50/1 (moles of methane/gram-atom S) to ¼, and preferably from about 20/1 to 1/1. In co-fed mode the volume of methane feed/volume of metal sulfide/hr can be from about 1,000 to 500,000 and preferably from about 3,000 to 50,000. It will be understood that NTP refers to room temperature (i.e. about 25° C.) and atmospheric pressure.

Examples of metal sulfides which may be used to convert methane include sulfides of the following elements zinc, titanium, tin, iron, nickel, rhenium, niobium, colbalt, sodium, potassium, magnesium, zirconium, vanadium, tantalum, chromium, molybdenum, tungsten, manganese, cadmium, yttrium and the lanthanides (i.e., lanthanum through lutetium).

EXAMPLES

A number of metal sulfides were used to convert methane. All of the metal sulfides used were purchased commercially from either Aldrich or Alfa and used as received. The metal sulfides were first sieved to 230/325 mesh, then 1.0 g of this sieved metal sulfide was dispersed on 4.0 g of 40/50 mesh, acid washed quartz. This dispersed metal sulfide was then loaded into a fritted, 17 mm od, quartz tubular reactor by adding a small amount of quartz to cover the frit, followed by the dispersed metal sulfide and more quartz (ca 16 g of additional quartz). The packed reactor was then placed in a furnace, and a gas manifold connected. Nitrogen was used to purge out the reactor for at least 20 minutes, followed by rapid heating of the reactor under nitrogen flow, to the required temperature. Next, the reactor exit was configured such that the effluent was collected into a plastic gas bag, while nitrogen (100 cc/min) was collected into it for 3-4 minutes. The reactor feed gas was then switched to a pure methane gas feed (150cc/min) for five minutes, followed by nitrogen (100 cc/min for 4 minutes). The contents of the gas bag were then analyzed by gas chromatography, and the conversions were calculated from the raw areas detected for methane and ethane. The presence of $H_2S$ in the product was confirmed by gas chromatography. The results are summarized in Table I.

TABLE I

Oxidative Coupling of Methane Using Metal Sulfides

| Metal Sulfide | Conversion (wt %) | Selectivity to Ethane (%) | Temperature (°C.) |
|---|---|---|---|
| ZnS | 1.40 | 100 | 850 |
| ZnS | 0.28 | 100 | 750 |
| TiS₂ | 0.65 | 100 | 850 |
| SnS₂ | 0.83 | 100 | 850 |
| Sm₂S₃ | 0.42 | 100 | 850 |
| FeS | 0.72 | 100 | 850 |
| NiS | 0.62 | 100 | 850 |
| ReS₂ | 0.93 | 100 | 850 |
| NbS₂ | 0.25 | 100 | 850 |
| CoS | 2.30 | 100 | 850 |

Reaction Conditions: 1.0 g of sieved metal sulfide (230/325 mesh) was used. All reactions were done by passing first nitrogen, then methane, followed by more nitrogen, at the indicated temperature. For al runs 750 cc $CH_4$/ cc metal sulfide/minute was employed.

What is claimed is:

1. A process for converting methane to at least one hydrocarbon having at least two carbon atoms, said process comprising contacting methane in the absence of $O_2$ with a reducible metal sulfide oxidizing agent under conditions sufficient to (i) produce said hydrocarbon and (ii) produce hydrogen sulfide.

2. A process according to claim 1, wherein natural gas is contacted with said metal sulfide.

3. A process according to claim 1, wherein the reaction conditions include a temperature of from about 400 to about 1000° C. and a pressure of from about 0.1 to about 30 atmospheres.

4. A process according to claim 1, wherein said metal sulfide is a sulfide of an element selected from the group consisting of zinc, titanium, tin, iron, nickel, rhenium, niobium, colbalt, sodium, potassium, magnesium, zirconium, vanadium, tantalum, chromium, molybdenum, tungsten, manganese, cadmium, yttrium and the lanthanides.

5. A process according to claim 1, wherein the reduced metal sulfide is regenerated.

6. A process according to claim 5, wherein the reduced metal sulfide is regenerated by oxidizing the reduced metal sulfide with elemental sulfur.

7. A process according to claim 6, wherein said elemental sulfur is produced by reacting said hydrogen sulfide with oxygen.

8. A process according to claim 1, wherein a sulfur-atom donor is co-fed along with said methane for contact with said metal sulfide.

* * * * *